(12) United States Patent
Huang et al.

(10) Patent No.: US 8,534,139 B2
(45) Date of Patent: Sep. 17, 2013

(54) BINDING FORCE TESTING DEVICE

(75) Inventors: Teng-Tsung Huang, New Taipei (TW); Yong-Bing Hu, Shenzhen (CN); Gong-Shui Cheng, Shenzhen (CN); Zhan Shang, Shenzhen (CN); Zhang-Sheng Yan, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 266 days.

(21) Appl. No.: 13/207,157

(22) Filed: Aug. 10, 2011

(65) Prior Publication Data
US 2012/0240690 A1   Sep. 27, 2012

(51) Int. Cl.
*G01L 5/00* (2006.01)
*G01L 1/22* (2006.01)
*G01N 3/20* (2006.01)
*G01N 3/22* (2006.01)
*G01N 3/08* (2006.01)
*G01N 19/04* (2006.01)

(52) U.S. Cl.
USPC ........... 73/862.01; 73/862; 73/150 A; 73/834; 73/838; 73/842; 73/845; 73/851; 73/848

(58) Field of Classification Search
USPC ................. 73/862.01, 862, 150 A, 838, 834, 73/851
See application file for complete search history.

(56) References Cited

U.S. PATENT DOCUMENTS

| | | | | |
|---|---|---|---|---|
| 5,176,028 A | * | 1/1993 | Humphrey | 73/150 A |
| 2005/0172730 A1 | * | 8/2005 | Hasegawa | 73/859 |
| 2010/0139385 A1 | * | 6/2010 | Ruminski | 73/150 R |

FOREIGN PATENT DOCUMENTS

| | | | |
|---|---|---|---|
| CN | 201072434 Y | * | 6/2008 |
| CN | 201917491 U | * | 8/2011 |

* cited by examiner

*Primary Examiner* — Lisa Caputo
*Assistant Examiner* — Jamel Williams
(74) *Attorney, Agent, or Firm* — Altis Law Group, Inc.

(57) ABSTRACT

A binding force testing device for testing the binding force of a hinge, includes a control chassis for controlling the binding force testing device; a platform mounted on the control chassis; a support mounted on the control chassis above the platform; a first driving device mounted on the support; a main holder mounted on the first driving device facing the platform; and a second driving device mounted on the support and connected to the first driving device. The first driving device drives the main holder to move relative to the platform in a first direction; the second driving device drives the first driving device to move relative to the platform in a second direction perpendicular to the first direction.

10 Claims, 3 Drawing Sheets

BINDING FORCE TESTING DEVICE

BACKGROUND

1. Technical Field

This disclosure relates to binding force testing devices, particularly to binding force testing devices for testing the binding force between two bonded parts of an electronic device.

2. Description of Related Art

The binding force value is an important parameter between two bonded parts of an electronic device, such as mobile phones or palm computers. Thus, the binding force of the two bonded parts must be tested in the manufacturing procedure. However, typically the testing of the binding force of the two bonded parts is done manually, which makes it difficult to get a precise value of the binding force.

Therefore, there is a room for improvement in the art.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the exemplary binding force testing device. Moreover, in the drawings like reference numerals designate corresponding parts throughout the several views. Wherever possible, the same reference numbers are used throughout the drawings to refer to the same or like elements of an embodiment.

DETAILED DESCRIPTION

Figure 1:
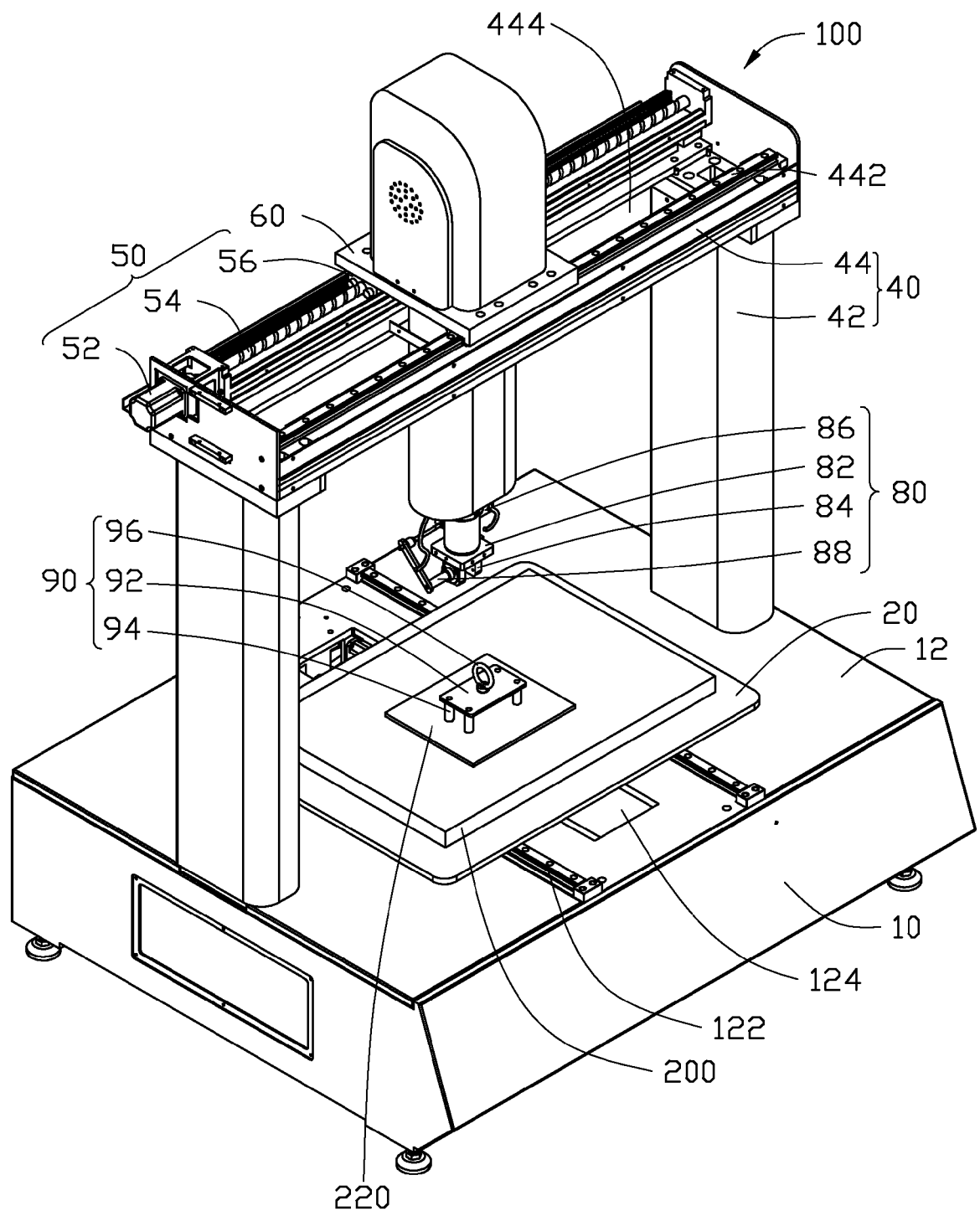
FIG. 1 is a schematic view of an exemplary embodiment of a binding force testing device.
Figure 2:
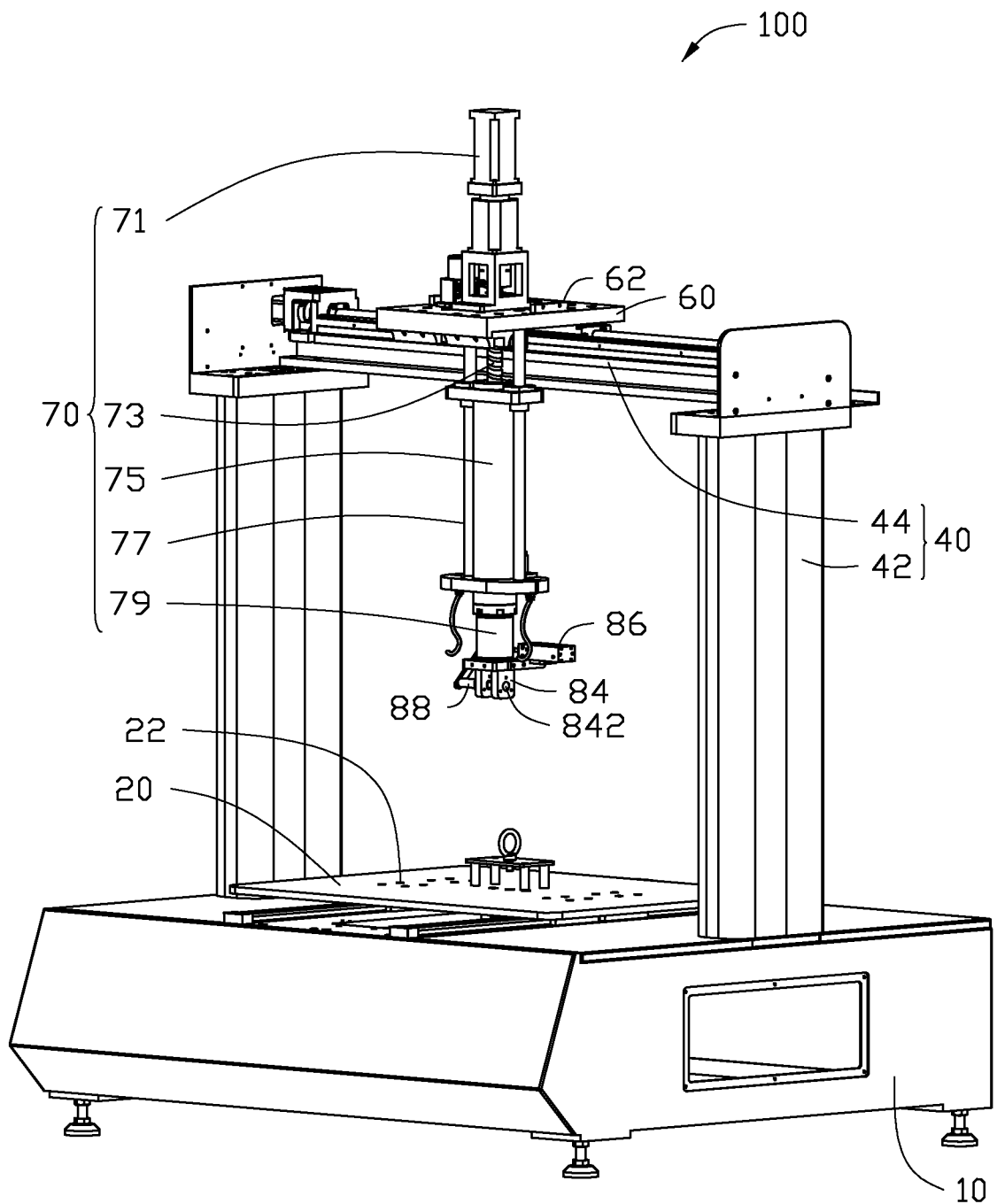
FIG. 2 is similar to the FIG. 1, but taken from another aspect and a protection cover is removed from the binding force testing device.
Figure 3:
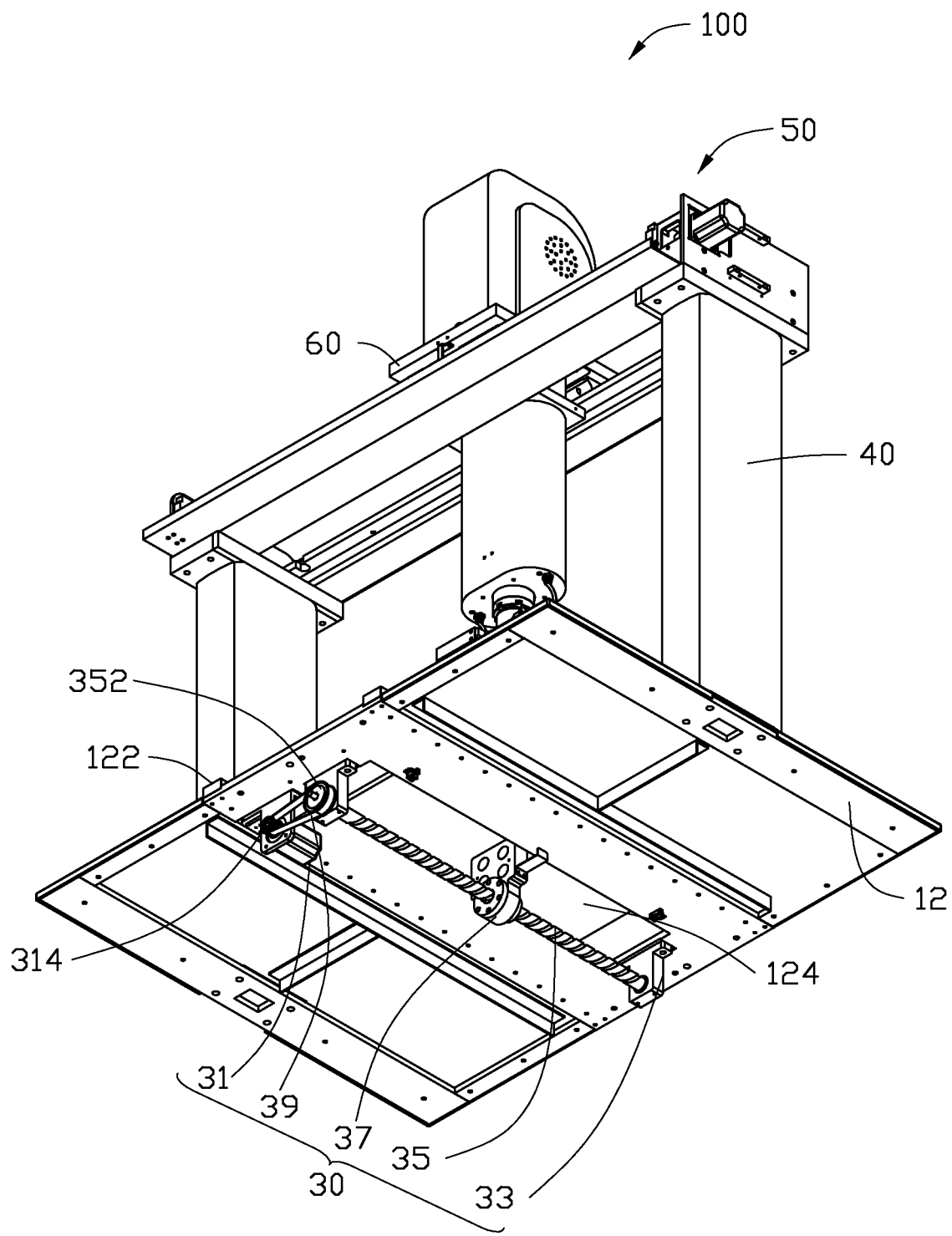
FIG. 3 is similar to the FIG. 1, but taken from another aspect with a control chassis removed from the binding force testing device.

Referring to FIGS. 1-3, an exemplary embodiment of a binding force testing device 100 for measuring binding force between a housing 200 and an additional element 220 is shown. The binding force testing device 100 includes a control chassis 10. A platform 20 mounted on the control chassis 10. A support 40 mounted on the control chassis 10 above the platform 20. A joint assembly 60 movably mounted on the support 40. A first driving device 70 (shown in FIG. 2) mounted on the joint assembly 60. A second driving device 50 mounted on the support 40. A third driving device 30 (shown in FIG. 3) mounted in the control chassis 10, and a main holder 80 mounted on the first driving device 70. The binding force testing device 100 may further include an assistant holder 90 to assist the main holder 80 to hold the additional element 220.

The control chassis 10 is used to control the binding force testing device 100. The control chassis 10 includes a top board 12 which has two first guiding rails 122 protruding in a first direction. The platform 20 is movably mounted on the first guiding rails 122 so the platform 20 can move relative to the control chassis 10 along the first guiding rails 122 in the first direction. The top board 12 further defines a guiding hole 124 between the first guiding rails 122 so the third driving device 30 can pass through the top board 12 to connect to and drive the platform 20. The platform 20 further defines a plurality of positioning holes 122 for positioning the housing 200.

The support 40 includes two posts 42 mounted on the top board 12, and a connecting rod 44 connecting the posts 42. The connecting rod 44 has two second guiding rails 442 protruding in a second direction perpendicular to the first direction. The connecting rod 44 further defines an opening 444 between the second guiding rails 442.

Referring to FIG. 2, the first driving device 70 includes a first motor 71, a first threaded rod 73, a first movable element 75, two guiding rods 77 and a connecting element 79. The first motor 71 is mounted on a surface of the joint assembly 60. The first threaded rod 73 is linked to the first motor 71 and passes through the joint assembly 60. The guiding rods 77 are mounted on another surface of the joint assembly 60 opposite to the first motor 71 in a third direction perpendicular to the first direction and the second direction. The first movable element 75 is threaded on the first threaded rod 73 and is movably mounted on the guiding rods 77. The connecting element 79 is mounted on a distal end of the first movable element 75.

The second driving device 50 includes a second motor 52 mounted on the connecting rod 44, a second threaded rod 54 is linked to the second motor 52, a second movable element 56 is threaded on the second threaded rod 54. The second movable element 56 is retained on the joint assembly 60 and is movably mounted on one of the second guiding rails 442. When the second motor 52 drives the second threaded rod 54 to rotate, the second movable element 56 moves along the corresponding second guiding rail 442 so both the joint assembly 60 and the first driving device 70 move relative to the platform 20 in the second direction.

Referring to FIG. 3, the third driving device 30 drives the platform 20 to move relative the control chassis 10 along the first guiding rails 122. The third driving device 30 includes a third motor 31 mounted on the control chassis 10. Two opposite seats 33 are mounted on the control chassis 10, a third threaded rod 35 is rotatably mounted on the seats 33, a third movable element 37 is threaded on the third threaded rod 35 and positioned in the guiding hole 124, and a belt 39 connects the third motor 31 with the third threaded rod 35. The third motor 31 includes a motor shaft 314. Each end of the third threaded rod 35 is rotatably mounted on one of the seats 33. The third threaded rod 35 may further include a pulley 352 located at one end adjacent to the third motor 31. The motor shaft 314 is connected to the pulley 352 with the belt 39 so the motor shaft 314 can drive the pulley 352 and the third threaded rod 35 to rotate. The third movable element 37 is retained on the platform 20, when the third threaded rod 35 rotates, the third movable element 37 can move in the guiding hole 124 to drive the platform 20 to move relative to the control chassis 10.

The joint assembly 60 includes a sliding board 62 retained on the second movable element 56 so the sliding board 62 can move in unison with the second movable element 56.

The main holder 80 includes a base 82 retained on the connecting element 79, two jaws 84, a holder control cylinder 86 and a pin 88 connecting to the holder control cylinder 86. Each jaw 84 defines a locking hole 842. The pin 88 can pass through or be removed from the holder control cylinder 86, to hold or release the assistant holder 90.

The assistant holder 90 includes a main body 92, a number of retaining elements 94 located on one surface of the main body 92 and a ring 96 located on an opposite surface of the main body 92. The retaining elements 94 are used to hold the additional element 220, the ring 96 is used to cooperate with the pin 88 to connect the main holder 80 to the assistant holder 90.

Referring to FIGS. 1-3, in use, the retaining elements 94 are retained on the additional element 220, with a vacuum attachment or magnetic force attachment. The housing 200 is retained on the platform 20. The third motor 31 is started to drive the third threaded rod 35 to rotate by the transition of the belt 39. Because the third movable element 37 is located in the guiding hole 124, the third movable element 37 cannot rotate with the third threaded rod 35, but can move in the guiding hole 124 to drive the platform 20 to move in the first direction, until the housing 200 is aligned with the opening 444 of the support 40. The second motor 52 is started, because the second movable element 56 is limited by the second guiding rail, the second movable element 56 cannot rotate with the second threaded rod 54. However, second movable element 56 can move relative to the second threaded rod 54 to drive the joint assembly 60 to move in the second direction, until the main holder 80 is aligned with the ring 96. The first motor 71 is started, because the guiding rod 77 limits the first movable element 75, the first movable element 75 cannot rotate with the first threaded rod 73. However, the first movable element 75 can move relative to the first threaded rod 73 to drive the main holder 80 to move in the third direction, until the jaws 84 are located at two sides of the ring 96. The holder control cylinder 86 is started to drive the pin 88 to pass through the jaws 84 and the ring 96. The first motor 71 is reversely started to drive the first movable element 75 to move in a fourth direction opposite to the third direction, causing the main holder 80, the assistant holder 90 and the additional element 220 to move away from the housing 200, thereby the assistant holder 90 applies a pulling force to the additional element 220. The pulling force is a predetermined value, which is equal to a required binding force between the additional element 220 and the housing 200. If the additional element 220 is still retained on the housing 200 after the pulling force is applied to the additional element 220, the binding force between the additional element 220 and the housing 200 satisfies testing requirement.

In the above exemplary embodiment, the binding force between the additional element 220 and the housing 200 can be tested by the binding force testing device 100, so can avoid using the typical manual way to test the binding force, thereby it is easy to get a precise value of the binding force between the additional element 220 and the housing 200.

It is to be further understood that even though numerous characteristics and advantages of the exemplary embodiments have been set forth in the foregoing description, together with details of structures and functions of various embodiments, the disclosure is illustrative only, and changes may be made in detail, especially in matters of shape, size, and arrangement of parts within the principles of the exemplary invention to the full extent indicated by the broad general meaning of the terms in which the appended claims are expressed.

What is claimed is:

1. A binding force testing device for testing the binding force of two combined components, the binding force testing device comprising:
   a control chassis for controlling the binding force testing device;
   a platform mounted on the control chassis, and one of the combined components being retained on the platform;
   a support mounted on the control chassis above the platform;
   a first driving device mounted on the support;
   a main holder mounted on the first driving device facing the platform; and
   a second driving device mounted on the support and connected to the first driving device;
   wherein the first driving device drives the main holder to move relative to the platform in a first direction and the second driving device drives the first driving device to move relative to the platform in a second direction perpendicular to the first direction so as to adjust the position of the main holder relative to the combined components to hold the other one of the combined components to the main holder, and the first driving further applying a predetermined pulling force to separate the combined components.

2. The binding force testing device of claim 1, further comprising a sliding board which connects the first driving device to the second driving device.

3. The binding force testing device of claim 2, wherein the first driving device comprises a first motor, a first threaded rod, a first movable element and a guiding rod; the first motor is retained on a surface of the sliding board opposite to the platform to drive the first thread rod to rotate, the first threaded rod is connected to the first motor and passes through the sliding board; the guiding rod is retained on another surface of the sliding board opposite to the first motor; the first movable element is screwed on the first threaded rod and is movably mounted on the guiding rod, and the main holder is mounted on the first movable elements.

4. The binding force testing device of claim 1, wherein the support comprises two posts retained on the control chassis and a connecting rod connecting the posts; and the second driving device is retained on the connecting rod.

5. The binding force testing device of claim 4, wherein the connecting rod has two second guiding rails both connects between the two posts and an opening defined between the two second guiding rails; and the second driving device is mounted on the second guiding rail, the first driving device passing through the opening.

6. The binding force testing device of claim 5, wherein the second driving device comprises a second motor mounted on the connecting rod, a second threaded rod linked to the second motor, a second movable element screwed on the second threaded rod; the second movable element is retained on the first driving device and movably mounted on one of the second guiding rail; when the second motor drives the second threaded rod to rotate, the second movable element and the first driving device moves along the second guiding rails.

7. The binding force testing device of claim 1, further comprising a third driving device received in the control chassis, the third driving device drives the platform to move relative to the control chassis in a third direction perpendicular to the first direction and the second direction.

8. The binding force testing device of claim 7, wherein the third driving device comprises a third motor mounted on the control chassis, two opposite seats mounted on the control chassis, a third threaded rod rotatably mounted on the seats, a third movable element screwed on the third threaded rod and a belt connecting the third motor with the third threaded rod; and the third threaded rod is retained on the platform, the third motor drives the third threaded rod to rotate so the platform moves in the third direction.

9. The binding force testing device of claim 8, wherein the control chassis comprises a top board on which the two seats are mounted, and a guiding hole defined therethrough, the third movable element is slidably located in the guiding hole to prevent the third movable element from rotating with the third threaded rod.

10. The binding force testing device of claim 1, wherein the main holder comprises two jaws, a holder controlling cylinder and a pin connecting to the holder controlling cylinder; each jaw defines a locking hole, the pin is driven to pass through or remove from the locking holes by the holder controlling cylinder.

\* \* \* \* \*